United States Patent [19]
Chieng

[11] Patent Number: 5,200,507
[45] Date of Patent: Apr. 6, 1993

[54] METHOD OF SEPARATING A PEPTIDE FROM A RESIN

[75] Inventor: Paul C. Chieng, St. Louis, Mo.

[73] Assignee: Mallinckrodt Specialty Chemicals Company, St. Louis, Mo.

[21] Appl. No.: 684,286

[22] Filed: Apr. 12, 1991

[51] Int. Cl.$^5$ .................. A61K 37/02; C08F 283/00
[52] U.S. Cl. .................. 530/344; 530/334; 525/54.11
[58] Field of Search .................. 530/334, 344; 525/54.11, 54.1

[56] References Cited

U.S. PATENT DOCUMENTS 4,130,514 12/1978 Enkoji et al. .................. 530/334
4,824,937 4/1989 Deghenghi et al. .................. 530/326

FOREIGN PATENT DOCUMENTS 0331073 9/1989 European Pat. Off. .

OTHER PUBLICATIONS

Nomizu et al., "Two-step hard acid deprotection/cleavage procedure for solid phase peptide synthesis", Int. J. Peptide Protein Res. 37, 1991 pp. 145-152.
Steward et al., Solid Phase Peptide Synthesis, 2nd Edition, Pierce Chemical Co., pp. 1-8, 38-40, 78-83, 89, 125-127 (1984).
Balasubramaniam et al., Synthesis of Neuropeptide Y, Int. J. Peptide Res., vol. 29, pp. 78-83 (1987).
Balasubramaniam et al., Syntheses and Receptor Affinities of Partial Sequences of Peptide YY (PYY), Peptide Research, vol. 1, pp. 32-35 (1988).
Barany et al., The Peptides, vol. 2, Eds. Gross and Meienhofer, Academic Press, Inc., pp. 65-77 (1980).
Horiki et al., Synthesis of the Merrifield Resin Esters of N-Protected Amino Acids with the Aid of Hydrogen Bonding, Chemistry Letters, pp. 165-168.
Wang et al., Enhancement of Peptide Coupling reactions by 4-Dimethylaminopyridine, Int. J. Peptide Res., vol. 18, pp. 459-467 (1981).
Multiple Peptide Systems advertisement (undated).

Primary Examiner—Lester L. Lee
Assistant Examiner—Bennett M. Celsa
Attorney, Agent, or Firm—Rothwell, Figg, Ernst & Kurz

[57] ABSTRACT

In solid phase peptide synthesis, resin-bound peptide is treated with hydrogen fluoride so as to cleave the peptide from the resin and form a first mixture of peptide, hydrogen fluoride and resin. The resin is removed from the first mixture so as to provide a resin-free second mixture including the polypeptide and the hydrogen fluoride. The polypeptide of the second mixture then is separated from the hydrogen fluoride.

12 Claims, No Drawings

METHOD OF SEPARATING A PEPTIDE FROM A RESIN

BACKGROUND OF THE INVENTION

1. Field of the Invention

The present invention relates to the field of separating a peptide from a resin to which the peptide is bonded, following solid phase peptide synthesis.

2. Description of the Background Art

Solid phase peptide synthesis involves assembling amino acids into a peptide of any desired sequence while one end of the chain is anchored to an insoluble support. The insoluble support is a synthetic polymer which bears reactive groups. The amino acid which forms the C-terminal reside of the peptide to be synthesized is converted to a derivative in which its amino group is protected by a labile protecting group. The derivative of the C-terminal amino acid is coupled to the reactive polymer. A reagent is applied to the protected aminoacyl polymer to remove the labile blocking group from the amino acid residue. The reagent must not harm the link of the C-terminal residue to the polymer in any way. Moreover, if the amino acid attached to the polymer contains a side-chain reactive functional group, that functional group must be blocked by a stable blocking group which will remain completely intact throughout the synthesis, but which can be removed finally to yield the free peptide. Following removal of the labile protecting group, the next amino acid is coupled to the aminoacyl polymer by use of a suitable coupling reaction. Again, the α-amino group must be protected with a labile protecting group. This cycle of deprotection and coupling is then repeated with each amino acid which is to be incorporated into the peptide chain. Finally, after the entire blocked peptide has been assembled on the polymer support, a different type of reagent is applied to cleave the peptide from the polymer and allow it to be dissolved. The blocking groups which have protected side-chain functional groups must also be removed, and usually are chosen so that they can be removed simultaneously with cleavage of the peptide from the resin.

One reagent for cleavage of peptide from the resin at the end of the synthesis is anhydrous liquid hydrogen fluoride (HF). HF cleavage is generally done at 0° C. for 30 minutes. Such conditions will generally cleave the peptide effectively from the resin and remove all side-chain blocking groups. The HF then is removed, e.g., under vacuum, and the cleaved peptide then is separated from the resin.

A common problem associated with HF cleavage of resin-peptide following solid phase peptide synthesis is side reactions caused by prolonged contact of the peptide with HF. In order to avoid "bumping", or a sudden surge of HF/resin slurry, the process is carried out very slowly, thereby prolonging the exposure of peptide to HF and causing the above-noted side reactions. The problem is even more pronounced in a large scale cleavage, e.g., greater than one liter, when a large quantity of HF cannot rapidly be removed after a proper reaction time has elapsed. Furthermore, constant monitoring and adjustment of vacuum level are required to control the process.

After removal of HF, the peptide is extracted from the resin with appropriate solvent(s). However, the low solubility of some peptides makes it difficult to completely recover the peptide from the resin, resulting in a lower yield.

There thus remains a need in the art for improved methods of separating peptides from resins so as to reduce or eliminate side reactions.

SUMMARY OF THE INVENTION

In accordance with the present invention, a method of separating a peptide from a resin to which the peptide is bound comprises treating the resin-bound peptide with hydrogen fluoride so as to cleave the peptide from the resin and form a first mixture of peptide, hydrogen fluoride and resin. The resin is removed from the first mixture so as to provide a resin-free second mixture including the polypeptide and the hydrogen fluoride. The polypeptide of the second mixture then is separated from the hydrogen fluoride present therein.

DETAILED DESCRIPTION OF THE PREFERRED EMBODIMENTS

The present invention is applicable to the well-known technique of solid phase peptide synthesis such as is described in Steward and Young, *The Chemistry of Solid Phase Peptide Synthesis*, Pierce Chemical Company (1984).

Peptides are formed in solid phase peptide synthesis on a resin support, such as 1% cross-linked polystyrene (copolymer of styrene with 1% divinylbenzene), MBHA, BHA, Pam resins and the like. Construction of the peptide is initiated by attaching to the resin a first amino acid which will form the C-terminal residue of the peptide to be synthesized. For example, the polystyrene resin beads can be functionalized by chloromethylation, which introduces benzyl chloride-type groups into the polymer. These halogens are reactive and when treated with the salt of a protected amino acid will form an ester, linking the protected amino acid covalently to the resin as a substituted benzyl ester.

Typically, the α-amino function of the amino acid is protected by a Boc group. After bonding of the initial amino acid to the resin, the Boc protecting group is removed by treatment with, for example, dilute solutions of strong acids such as 25% trifluoroacetic acid (TFA) in dichloromethane (DCM). After removal of the Boc protecting group, the newly exposed amino group is present as an acid salt which can be converted to a free base by treatment with a tertiary amine, such as triethyl amine in DCM.

The peptide is then "grown" by sequentially coupling Boc protected amino acids to the aminoacyl resin, typically by use of dicyclohexylcarbodiimide (DCC), with each additional amino acid being added after removal of the Boc-group from the last amino acid in the chain. Following completion of assembly of the desired blocked peptide on the resin, the resin-bonded peptide can be treated with anhydrous HF to cleave the linkage of the peptide to the resin in order to liberate the free peptide.

In accordance with one embodiment of the present invention, the resin-bonded peptide is treated with hydrogen fluoride at a cleavage temperature of from about −5° C. to about 5° C. for from about one-half hour to about one hour so as to cleave the peptide from the resin with the peptide substantially intact.

After cleaving the peptide from the resin and thereby forming a mixture containing resin, cleaved peptide and hydrogen fluoride, the mixture is quickly filtered to remove the resin, leaving HF and peptide remaining in the filtrate.

Since peptides are soluble in HF, the majority of the cleaved peptide remains in the filtrate, and can be separated from the HF by, for example, vacuum distillation of the HF from the filtrate.

After removal of the HF from the filtrate, the peptide present in the residue can be washed with a solvent in which HF is soluble and the peptide is insoluble, so as to remove residual HF from the distillation residue. Suitable solvents for washing the peptide include diethyl ether and ethyl acetate.

Any cleaved peptide remaining with the resin subsequent to filtration and vacuum distillation can be separated from the resin by repeating the HF extraction as described above, or by methods well known in the art, such as by extraction with acetic acid.

The invention is further illustrated by the following examples, which are not intended to be limiting.

EXAMPLE I

A resin-bonded tetrapeptide (leu-Ala-Gly-Val-Pam-resin) was cleaved with HF at 0° C. for one-half hour in a teflon reactor. At the end of the cleavage, the peptide/resin/HF slurry was filtered through a pre-chilled teflon filter into a container. The HF filtrate was evaporated under vacuum, and after 15 minutes, a faint, white film was found deposited on the container wall. This film was extracted with ethyl acetate (EtOAc)/1M acetic acid (HOAc) (15 ml each). The aqueous phase was collected from a separatory funnel and lyophilized. The resin which had been removed from the filtrate was washed with EtOAc and extracted with HOAc. Crude peptide present in the resin-derived extract was lyophilized. The total crude peptide recovered from both the filtrate and the resin was 148.4 milligrams per gram peptide resin, with 96% recovered from the HF filtrate and 4% from the resin.

EXAMPLE II

Resin bound Desmopressin-MBHA (20.6 gm) was swollen with 20 ml anisole and brought to contact with anhydrous HF (200 ml) at 0° C. for one hour. The peptide/HF solution was filtered into a Teflon evaporator. Another 100 ml HF was charged into cleavage reactor and filtered into the same Teflon evaporator. HF was removed by vacuum distillation. No bumping was observed during the distillation even though a full vacuum was applied. At the end of the distillation, a sticky, light brown mass of crude peptide was obtained. After repeated washing with ethyl ether, the crude peptide became less sticky and the color turned to light yellowish. The mass was estimated to be 12–14 gram. The resin, after being washed with ethyl ether, was extracted with 1 M acetic acid solution. No measurable quantity of peptide, however, was obtained from the resin which suggest that the peptide had been completely extracted with HF.

The prior art problems of "bumping" and prolonged exposure of peptide to HF causing undesired side reactions are eliminated by separating HF from resin after the cleavage reaction is completed. The separation of HF and resin can be achieved by filtration, centrifugation or any other means of separating liquid from solid. The HF then can be removed by vacuum distillation in the absence of resin beads. Without being bound to any particular theory, it is believed that with the present invention, where the solid particles are very small in the slurry and the consistency is very high, the slurry displays properties, such as viscosity, that are quite different from those of true liquids. It is this non-Newtonian behavior that is believed to cause the "bumping" problem in prior art HF removal from resin beads.

By removing resin prior to separating HF from peptide in accordance with the present invention, several significant advantages are achieved. A high vacuum can be applied for separation of HF without causing any "bumping" problem. HF is removed at a higher rate, thus reducing the contact time between HF and peptide. Because there is no "bumping" problem, a large scale process is easy to operate.

Additionally, HF is one of the best solvents for peptide. Therefore, by using HF both as a cleavage reagent and as an extractant for peptide, the yield for some "insoluble" peptides is improved.

After HF is removed from the filtrate, the crude peptide can be effectively washed with a suitable solvent to remove small organic impurities. The solid crude peptide obtained in this manner may offer an opportunity for purification in that it may be crystalized in an appropriate solvent. Thus, a final HPLC purification step may be improved or even eliminated.

Furthermore, the low-high HF cleavage method proposed by Tam, et al., *Peptide Research* 1:6 (1988), can be greatly improved by utilization of the present invention, if the solid polymer support used is MBHA, BHA or Pam resin. The low-high HF scheme proposed by Tam, et al. calls for a vacuum distillation of low-HF (DMS/HF/scavenger) which may take hours to accomplish, before proceeding to the high-HF (scavenger/HF) step. By utilization of the present invention, the HF under low-HF conditions can be easily filtered off from the reaction vessel and additional amounts of HF can be charged into the reactor to effect the final cleavage of peptide from resin under high-HF conditions.

The present invention minimizes contact time between the peptide and the HF, and HF remaining after vacuum distillation is diluted by the charged solvent so as to further reduce side-reactions. If desired, the peptides can be repeatedly washed before being dried and no lyophilization is needed to obtain dry peptide powder. The peptide powder can easily be stored in a freezer, and the peptide in dry powder form allows better process control of subsequent purification steps.

The present invention provides an effective method for reducing the side reaction problems associated with HF cleavage of resin-bonded peptides. Since many modifications, variations and changes in detail may be made to the described embodiments, it is intended that all matter in the foregoing description be interpreted as illustrative and not in a limiting sense.

What is claimed is:

1. A method of separating a peptide from a resin to which the peptide is bound, comprising the steps of
   a) treating the resin-bound peptide with hydrogen fluoride so as to cleave the peptide from the resin and form a first mixture of peptide, hydrogen fluoride and resin;
   b) removing the resin from said first mixture so as to provide a resin-free second mixture including said peptide and said hydrogen fluoride; and
   c) separating the peptide of said second mixture from the hydrogen fluoride of said second mixture.

2. The method of claim 1 wherein the hydrogen fluoride treatment occurs at a temperature from about −5° C. to about 5° C.

3. The method of claim 1 wherein the resin-bound peptide is treated with hydrogen fluoride for a period of from about one-half hour to about one hour.

4. The method of claim 1 wherein the resin is removed from the first mixture by filtration.

5. The method of claim 1 wherein the peptide is separated from the hydrogen fluoride of the second mixture by vacuum distillation.

6. The method of claim 1, further including the step of washing the peptide separated in step c) with a solvent in which hydrogen fluoride is soluble and said peptide is insoluble.

7. The method of claim 6 wherein the solvent is diethyl ether or ethyl acetate.

8. The method of claim 1, further including the step of recovering any cleaved peptide remaining with the resin after said resin is removed from the first mixture.

9. The method of claim 8 wherein the remaining cleaved peptide is recovered by repeating steps a) through c).

10. The method of claim 8 wherein the remaining cleaved peptide is recovered by repeating steps a) through c), and further including the step of washing the peptide separated in step c) with a solvent in which hydrogen fluoride is soluble and said peptide is insoluble.

11. The method of claim 8 wherein the remaining cleaved peptide is recovered by extraction.

12. The method of claim 11 wherein the remaining cleaved peptide is extracted with acetic acid.

* * * * *